United States Patent [19]

Firester et al.

[11] 4,030,835
[45] June 21, 1977

[54] DEFECT DETECTION SYSTEM

[75] Inventors: Arthur Herbert Firester, Skillman; Istvan Gorog, Princeton, both of N.J.

[73] Assignee: RCA Corporation, New York, N.Y.

[22] Filed: May 28, 1976

[21] Appl. No.: 691,206

[52] U.S. Cl. .............................. 356/111; 250/550; 250/572; 356/237
[51] Int. Cl.$^2$ ...................................... G01N 21/32
[58] Field of Search .............. 250/237 G, 550, 571, 250/572; 350/162 R; 356/106 R, 109, 111, 200, 209, 237

[56] References Cited

UNITED STATES PATENTS

| | | | |
|---|---|---|---|
| 3,783,296 | 1/1974 | Blevins | 250/550 |
| 3,879,131 | 4/1975 | Cuthbert et al. | 250/572 X |
| 3,915,576 | 10/1975 | Taylor | 356/111 X |
| 3,992,111 | 11/1976 | Roulier et al. | 250/572 X |

*Primary Examiner*—John K. Corbin
*Assistant Examiner*—Matthew W. Koren
*Attorney, Agent, or Firm*—Eugene M. Whitacre; William H. Meagher; Henry N. Garrana

[57] ABSTRACT

Defect detection apparatus, for optically inspecting a spiral groove of a video disc record, directs a coherent light beam at the grooved surface of the disc. The incident beam, focused at a point beyond the disc surface, illuminates the grooved surface with a light spot that spans a plurality of convolutions of the groove. Relative motion is established between the disc surface and the incident beam in a manner causing the illuminating spot to rapidly scan the groove surfaces in a coarse spiral pattern. The structure of the illuminated groove convolutions, absent any defects, serves as a diffraction grating for diffracting the light into an undeviated zero diffraction order cone of light that converges at a first location in a plane spaced from the disc surface and into deviated higher diffraction order cones of light that converge at additional locations in said plane separated from the first location. A photodetector is positioned to be in registry with the first location and spaced from said additional locations. A blocking means is placed over a central region of the photodetector to normally intercept the zero diffraction order light, thereby preventing the conversion of light energy to electric energy by the photodetector when defect-free groove regions are illuminated. When a defect exists in the illuminated region of the groove, unblocked regions of the photodetector receive light and the photodetector produces electrical signals indicative of the presence of a defect. A servo means, responsive to departures of the zero order cone axis from a desired orientation, is employed for controlling the orientation of the axis of the incident beam to oppose such departures, in order to preclude false defect indications due to warpage or unevenness of the disc record.

8 Claims, 4 Drawing Figures

DEFECT DETECTION SYSTEM

The present invention relates generally to a novel system employing optical techniques for detecting defects in a regularly grooved surface, and particularly to defect detection systems and optical techniques therefor which may be employed to determine flaws in the spiral groove of a high density information record, such as a video disc of the type described in U.S. Pat. No. 3,842,194, issued to Jon K. Clemens.

The defect detection principles of the present invention are applicable to optical inspection of spiral grooves for video disc records at various manufacturing stages throughout the record mastering and replicating processes, i.e., both prior to the utilization of the groove as an information track, as well as after information has been recorded.

In one illustrative process of producing a video disc record having spiral grooves, a disc master (to be used for recording) is formed by (1) mechanically cutting a spiral groove of a trapezodial cross-section in a copper-coated aluminum disc, and (2) coating the grooved surface with electron beam sensitive material. The coated disc is mounted on a turntable of an electron beam disc recorder in the path of a finely focused beam of electrons, that is turned on and off in response to a recording signal, to expose various portions of the groove bottom as the disc is rotated and translated with respect to the impinging beam. Those portions of the groove bottom struck by the electron beam are removed by subsequent development of the sensitive material. After exposure and development, the master disc has the relief pattern that is desired for the final records. Molds for making stampers for producing production line records are made from these masters. In the final stages of manufacturing a video disc, a vinyl substrate is formed with the desired relief pattern, using a stamper made from a mold; the substrate is coated with a metal by a vacuum sputtering process; the metal is coated with a styrene dielectric by a glow discharge process; and the styrene is coated with a layer of oil by an evaporation process.

During each of the above-described manufacturing processes, various kinds of flaws, which affect the record groove, can develop which are difficult to detect, in view of the fineness of the groove structure typically employed in video discs (e.g., 5555 convolutions per inch). The present invention employs optical techniques to provide a system for rapidly identifying the presence of such flaws. Stains, scratches, burrs and coating defects are illustrative kinds of asperities which can be detected by this defect detector during record manufacture.

In accordance with the principles of the present invention, an optical system is provided for forming a light beam, using light from a coherent light source, and directing The beam at the grooved surface of the disc record. The incident light beam, focused at a point beyond the disc surface, illuminates the grooved surface with a light spot having a half-intensity contour that spans a plurality of groove convolutions. The axis of the incident beam path lies in a non-parallel relationship, and at a chosen angle (e.g., 45°), with respect to the central axis of the disc: the incident beam axis is desirably positioned in a plane which contains the disc's central axis and intersects the grooved surface along a radius of the disc (so that the beam axis is substantially perpendicular to a tangent to a groove convolution at the point of incidence).

The illuminated portion of the groove convolutions effectively forms a diffraction grating, which is uniform (in the absence of defects). The effect of the diffraction grating on light reflected from the grooved surface is to form a undeviated zero diffraction order cone of light converging at a given location in a plane spaced from the grooved surface and deviated higher diffraction order cones of light converging at additional locations in said plane which are separated from said given location. A photodetecctor is positioned so that its photosensitive surface is out of the paths of the higher diffraction order cones of light, but in registry with the path of the zero diffraction order cone of light. A portion of the photosensitive surface, upon which the zero diffraction order light would otherwise fall, is shielded from such light impingement by a light blocking means interposed in the path of the zero order cone.

Relative motion between the grooved surface and the incident beam is established in such manner that a succession of regions of the grooved surface are scanned by the incident light beam in a spiral pattern. Illustratively, the desired relative motion is established by rotating the disc at a first selected rate, while translating the rotating disc in a radial direction at a second selected rate. Through choice of the rates, the coarseness of the spiral scanning pattern may be controlled. Desirably, the rates are chosen so that the spiral light scanning pattern has a pitch appreciably greater than the disc's groove pitch, whereby the entire grooved surface of the disc may be scanned for defect detection purposes in a time period which is short (e.g., 3–5 minutes) relative to the normal playing time (e.g., 30 minutes) of the disc surface.

When defects in the grooved surface are illuminated, the uniform diffraction grating effect is disturbed and some light reflected from such a surface will fall upon the unblocked regions of the photosensitive surface of the photodetecctor, which produces an electrical signal output indicative of the defect presence.

Accurate positioning of the blocking means and the photodetector can insure that the unblocked regions of the photosensitive surface will not receive light when defect-free regions of the disc surface are illuminated (the zero diffraction order component being intercepted by the blocking means, and the higher diffraction order components bypassing the photodetector), if one can safely assume that the disc surface in which the groove convolutions appear is otherwise flat and maintains a constant attitude relative to the incident beam. However, this assumption cannot be made in all instances. For example, a replicated disc is likely, due to effects of the replication processes, to exhibit warpage to some degree. As the warped disc is rotated, the surface attitude of the regions being illuminated will be subject to variation, with resultant shifting of the locations of the respective diffraction order components. In the absence of compensation for the surface attitude changes, a false defect indication may be produced as a consequence of, for example, a shifting of one of the diffraction order components sufficient to cause its impingement upon the unblocked region of the photodetector surface.

Pursuant to a further feature of the present invention, compensation for the above-mentioned surface attitude changes may be effected by providing an optical servo system to alter the incident beam attitude in a manner opposing shifts in the locations of the diffraction order components.

The error information for this servo system is illustratively derived from a quadrant photodetector, upon which is centered a portion of the zero diffraction order light, diverted thereto by means of a beam splitter; and control of the incident beam attitude in response to such error information is illustratively effected by galvanometer controlled mirrors which control the orientation of the axis of the incident beam path.

The defect indicating output signals of the above-described defect detection system may be used in a variety of ways: e.g., as input to a meter, a counter, a recorder, etc. A particularly advantageous use of such defect indicating signals is as the input to a defect plotting system of the type disclosed in a copending application of Arthur Firester and Joseph Walentine, entitled, "Defect Plotting System", and concurrently filed herewith.

IN THE ACCOMPANYING DRAWINGS

Figure 1:
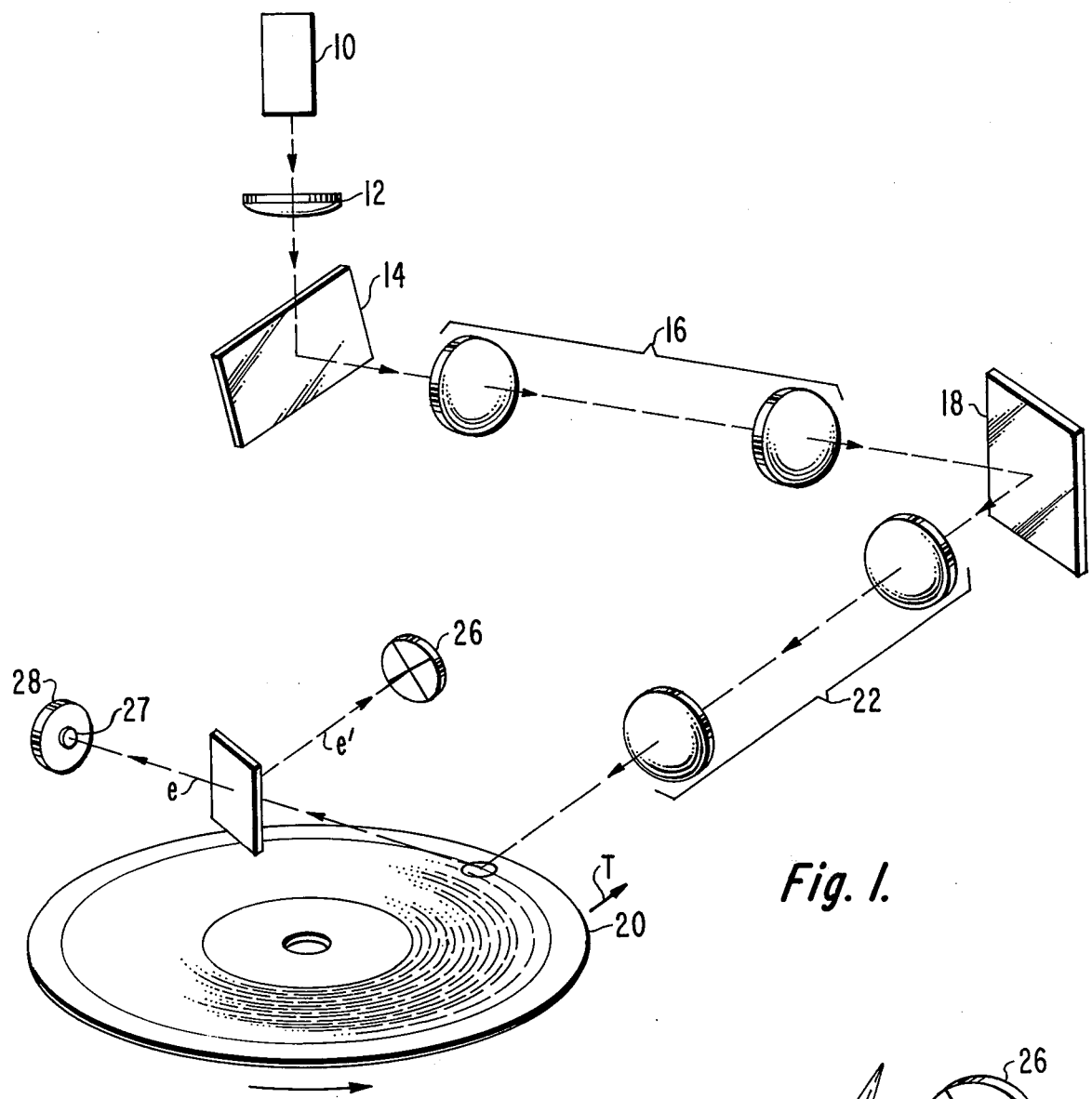
FIG. 1 illustrates, in a perspective view, a portion of a defect detection system embodying the principles of the present invention.

Referring to FIG. 1, a coherent light beam from a light source 10 (illustratively, in the form of a laser) is focused by a lens 12 toward a point beyond the reflecting surface of a first mirror 14. The converging beam impinging upon the mirror surface is reflected thereby toward a first relay lens 16. The beam transmitted by lens 16 is intercepted by the reflecting surface of a second mirror 18, and redirected thereby to pass toward the surface of a rotating disc record 20 via a second relay lens 22. The light beam emerging from relay lens 22 converges toward a focus point beyond the surface of record 20, forming a light spot at the intercepting surface region of such a size that a plurality of convolutions of the record's spiral groove (e.g., 30 convolutions of a 5555 convolution inch disc record) are illuminated. Rotating record 20 is translated in a radial direction T (by means not shown in FIG. 1), causing the illuminating light spot to scan the record surface in a coarse spiral pattern, having a pitch appreciably greater than the pitch of the spiral groove.

The orientation of the incident beam is desirably such that the axis of the incident beam lies in a non-parallel relationship, and at a chosen angle (e.g., 45°) with respect to the central axis of the record, and is substantially coplanar with said central axis in a plane which intersects the record surface along a radius of the record.

Light is reflected by the illuminated record surface region toward a beam splitter 24 (e.g., a partially silvered mirror). Beam splitter 24 permits a portion of the light it receives to pass toward a first photodetector 28, while reflecting the remainder toward a second photodetector 26.

The groove structure in the illuminated region, in the absence of defects, provides a regular pattern of depressions and elevations, which effectively serves as a diffraction grating (with a grating pitch determined by the groove convolution pitch) to diffract the light passing to the photodetectors in a fixed pattern. This light diffraction results in the formation of an undeviated zero diffraction order cone of light and a plurality of additional, deviated cones of light corresponding to higher diffraction orders.

Figure 2:
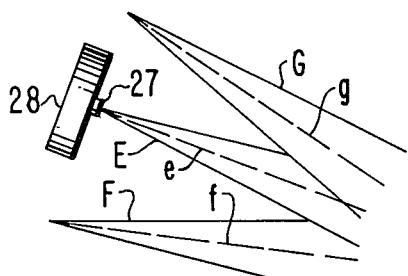
FIGS. 2 and 3 illustrate illumination patterns for respective photodetector elements of the FIG. 1 apparatus.

As shown in FIG. 2, an undeviated zero diffraction order cone (E) converges toward a point at the center of the photosensitive region of detector 28 while plus and minus first diffraction order cones (F and G) converge at points spaced from this photosensitive region, i.e., with the deviation of their axes $(f, g)$ being sufficient to cause the first diffraction order light to bypass detector 28. To prevent detector 28 from converting light energy to electric energy when normal groove structure is illuminated, a light blocking means 27 is disposed over the center region of detector 28 to intercept the zero diffraction order cone E. However, when defects disturb the regularity of the groove structure in an illuminated region, confinement of light to the aforesaid cones is no longer maintained, and the unblocked regions of the photosensitive surface of detector 28 will receive light energy, which is converted thereby to electrical energy signalling the illumination of a defect in the spiral groove.

Figure 3:
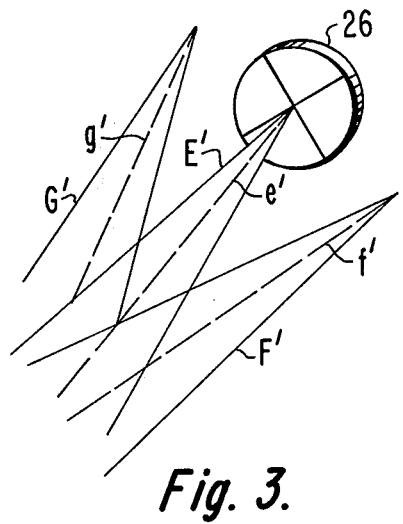

With reference to FIG. 3, the diffracted light that is diverted toward the photodetector 26 is illustrated. Normally, during illumination of defect-free record surface regions, deviated first diffraction order cones (F', G') bypass the photosensitive region of photodetector 26 while an undeviated zero order cone (E') impinges upon the center of the photosensitive region of detector 26. Illustratively, detector 26 contains four independent photosensitive cells disposed symmetrically about the center of the light accepting region. With appropriate biasing of the cells, by means not shown, individual voltage sources exist representative of the light energy received by each cell. When cone E' is properly centered on photodetector 26, the light energy received by each cell thereof is the same (this condition being indicative of the desired centering of cone E on the light blocking means 27, as shown in FIG. 2). Any miscentering of the cone E' with respect to detector 26 causes a departure from such coequal reception of light energy by the respective cells. By suitable matrixing of the voltages generated by the individual cells of photodector 26, error signals may be developed representative of the sense and magnitude of any such miscentering.

Figure 4:
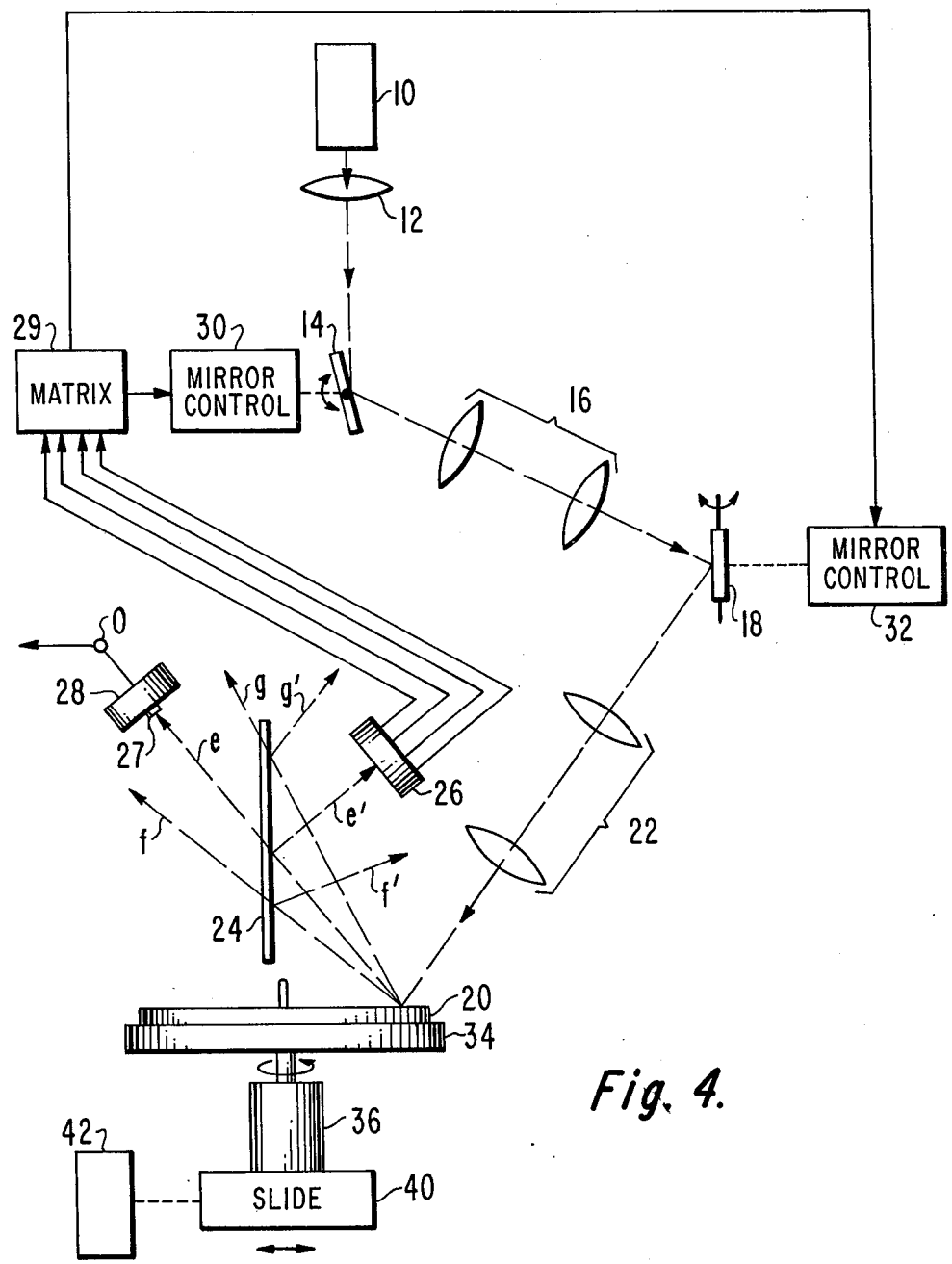
FIG. 4 illustrates a defect detection system, associating the FIG. 1 apparatus with control systems for beam orientation control, in accordance with a particular embodiment of the present invention.

A servo system for using such error signals to control the orientation of the light beam incident upon the surface of disc 20 is shown in FIG. 4 in association with the above-described apparatus of FIG. 1. For various reasons, such as warp, for example, regions of the disc surface may depart from desired flatness; the resultant surface attitude variations may cause false indications of groove defects unless compensation for such surface attitude variations are provided. The servo system provided in FIG. 4 achieves the desired compensation by suitably changing the incident beam orientation via control of the positions of movable mirrors 14 and 18.

Matrix circuits 29 respond to the four individual cell output voltages of quadrant photodetector 26 to develop: (1) a first error signal indicative of the sense and magnitude of any lateral departure of cone E' of FIG. 3 from the center of the light accepting region of quadrant photodetector 26; and (2) a second error signal indicative of the sense and magnitude of any vertical departure therefrom.

The first error signal is applied to mirror control circuit 32 to impart angular changes to the incident beam orientation in a direction to oppose undesired lateral direction movements of cones E' (FIG. 3) and E (FIG. 2), i.e., by causing movable mirror 18 to rotate an appropriate amount about an axis that is parallel with the center axis of the disc record 20. The second error signal is applied to mirror control circuit 30 to impart angular changes to the incident beam orientation in a direction to oppose undesired vertical direction movements of cones E' and E, i.e., by causing movable mirror 14 to rotate an appropriate amount about an axis that is perpendicular to the center axis of disc record 20.

By utilization of the error information to maintain cone E' properly centered on photodetector 26, compensation for the surface attitude changes is realized, the compensation preventing a spurious shift of cone E to an unblocked region of photodetector 28 by the altered surface attitude, thereby avoiding development of false defect indications at the output terminal (O) of photodetector 28.

A succession of regions of the grooved surface of record 20 are scanned by the incident beam in a spiral pattern when a desired relative motion between the surface of disc 20 and the beam is established. This desired motion is realized by rotating disc 20 on a turntable 34 driven by turntable motor 36 at a first selected rate, while translating disc 20 in a radial direction (e.g., through use of a suitable drive source 42 to effect translation of a slide 40 upon which the motor driven turntable 34 is supported. By selectively choosing these two rates, a desired coarseness of the spiral scanning pattern may be accomplished. Various degrees of overlap of the scanning pattern convolutions may be achieved. Desirably the two rates are chosen so that the spiral light scanning pattern has a pitch appreciably greater than the disc's grooved pitch so that the entire grooved surface may be scanned for defects in a time span appreciably shorter than the normal playing time for the disc.

What is claimed is:

1. A flaw detection system for detecting defects in a spiral groove formed in a surface of a disc, said system comprising:

means for illuminating a region of the grooved surface of said disc, the illuminated region being sufficiently large to span a plurality of convolutions of said spiral groove;

said illuminating means including means for forming a beam of light directed toward said surface along an incident beam path, and converging toward a point beyond said surface; the orientation of the axis of said path being normally such that said axis lies in non-parallel relationship, and at a chosen angle, with respect to the central axis of said disc in a first plane which intersects said surface along a radius of said disc;

the structure of the groove convolutions in the surface region illuminated by said light beam, absent any defects, serving as a diffraction grating for diffracting light reflected from said illuminated region to form an undeviated zero diffraction order cone converging at a first location in a second plane spaced from the grooved surface of said disc and deviated higher diffraction order cones of light respectively converging at additional locations in said second plane separated from said first location;

means for establishing relative motion between said grooved surface and said beam path in such manner that a succession of regions of said grooved surface are scanned by said light beam in a coarse spiral pattern having a pitch appreciably greater than the pitch of said spiral groove;

light detection means having a photosensitive surface substantially in registry with said first location in said second plane and separated from said additional locations;

light blocking means overlying only a selected portion of said photosensitive surface and positioned to intercept said zero diffraction order cone of light; and means responsive to signals developed by said light detection means for indicating illumination of a defect.

2. Apparatus in accordance with claim 1 also including means responsive to deviations of the orientation of the axis of said zero diffraction order cone of light from a desired orientation for controlling the orientation of the axis of said incident beam path in a manner opposing said deviations.

3. Apparatus in accordance with claim 2 wherein said orientation controlling means includes means for diverting a portion of said zero diffraction order cone of light towards a second location in a third plane different from said second plane containing said first location; an additional light detection means substantially in registry with said second location for deriving error information indicative of deviations of the axis of said zero diffraction order cone from said desired orientation; and means for utilizing said error information to vary said orientation of the axis of said incident beam path.

4. Apparatus in accordance with claim 3 wherein said diverting means comprises a beam splitter for allowing a portion of the light of said zero diffraction order cone to converge at said first location in said second plane while causing the remainder of the light of said zero diffraction order cone to converge at said second location in said third plane.

5. Apparatus in accordance with claim 3 wherein said additional light detection means includes a quadrant detector comprising two pairs of photosensitive elements mounted in a common housing and symmetrically disposed about the center of a light accepting region of said housing; said housing being disposed at said second location so that said light accepting region intercepts the diverted portion of said zero diffraction order cone, with said diverted light portion being centered upon said light accepting region center when said desired axis orientation is obtained; said two pairs of photosensitive elements providing electrical signals indicative of any miscentering of said diverted portion of said zero diffraction order cone when said desired axis orientation is not obtained; wherein said additional light detection means also includes means responsive to said electrical signals for providing error information to said error information utilization means for imparting angular changes to said incident beam so as to vary the angular relationship of the axis of said incident beam path with respect to the central axis of said disc about said chosen angle and/or to shift said incident beam path axis from said first plane so as to oppose said deviations of the orientation of the axis of said undeviated zero diffraction order cone from said desired orientation, whereby to substantially ensure maintenance of convergence of said zero diffraction order cone at said first location.

6. Apparatus in accordance with claim 5 wherein said error information utilization means comprises a first galvanometer controlled mirror disposed in the path of said incident light for varying the angular relationship between the axis of said incident beam path and said central axis, and a second galvanometer controlled mirror disposed at a different location in the path of said incident beam for effecting said incident beam path axis shifting from said first plane.

7. A method for detecting defects in a spiral groove formed in a surface of a disc which comprises:
   rotating said disc;
   forming a beam of light, directed toward the grooved surface of said rotating disc and converging toward a point beyond said surface to illuminate a region of said rotating disc spanning a plurality of convolutions of said spiral groove, while establishing relative translation between said grooved surface of said rotating disc and said beam in such a manner that a succession of regions of said grooved surface are scanned by said light beam in a coarse spiral pattern having a pitch appreciably greater than the pitch of said spiral groove;
   intercepting the zero diffraction order component of light diffracted by defect-free regions of said grooved surface when illuminated; and
   detecting the presence of light in a region surrounding the location of said zero diffraction order component interception.

8. A method in according with claim 7 wherein said light detecting is effected in a region separated from the locations of higher-than-zero diffraction order components of light diffracted by defect-free regions of said grooved surface when illuminated.

* * * * *